(12) United States Patent
Karwacki, Jr. et al.

(10) Patent No.: US 7,832,591 B2
(45) Date of Patent: Nov. 16, 2010

(54) METHODS AND APPARATUS FOR DISPENSING SOLID PHARMACEUTICAL ARTICLES

(75) Inventors: Edward Joseph Karwacki, Jr., Garner, NC (US); Richard D. Michelli, Raleigh, NC (US); David Newcomb, Morrisville, NC (US)

(73) Assignee: PARATA Systems, LLC, Durham, NC (US)

( * ) Notice: Subject to any disclaimer, the term of this patent is extended or adjusted under 35 U.S.C. 154(b) by 642 days.

(21) Appl. No.: 11/834,936

(22) Filed: Aug. 7, 2007

(65) Prior Publication Data

US 2008/0283543 A1 Nov. 20, 2008

Related U.S. Application Data

(60) Provisional application No. 60/938,835, filed on May 18, 2007.

(51) Int. Cl.
*G06F 7/00* (2006.01)

(52) U.S. Cl. .................... 221/7; 221/2; 700/231; 700/244

(58) Field of Classification Search .......... 700/231, 700/242–244; 221/2, 7
See application file for complete search history.

(56) References Cited

U.S. PATENT DOCUMENTS

| | | | |
|---|---|---|---|
| 2,665,775 A | 1/1954 | Smith |
| 2,708,996 A | 5/1955 | Skillman |
| 2,865,532 A | 12/1958 | Smith |
| 3,023,851 A | 3/1962 | Stiller |
| 3,144,958 A | 8/1964 | Gumpertz |
| 3,160,793 A | 12/1964 | Colburn |
| 3,179,288 A | 4/1965 | Davy |
| 3,185,851 A | 5/1965 | D'Emilio |
| 3,196,276 A | 7/1965 | Naab |
| 3,206,062 A | 9/1965 | Rappaport |
| 3,310,199 A | 3/1967 | Roberts |
| 3,312,372 A | 4/1967 | Cooper, Jr. |
| 3,410,450 A | 11/1968 | Fortenberry |
| 3,417,542 A | 12/1968 | Merrill |
| 3,436,736 A | 4/1969 | Platt |
| 3,556,342 A | 1/1971 | Guarr |
| 3,599,152 A | 8/1971 | Williams |
| 3,653,176 A | 4/1972 | Gess |

(Continued)

FOREIGN PATENT DOCUMENTS

CA 936 501 11/1973

(Continued)

*Primary Examiner*—Gene Crawford
*Assistant Examiner*—Michael K Collins
(74) *Attorney, Agent, or Firm*—Myers Bigel Sibley & Sajovec, PA

(57) ABSTRACT

A method is provided for dispensing solid pharmaceutical articles using an apparatus including a housing and a sensor system, the housing defining a dispensing passage having a dispensing inlet and a dispensing outlet downstream of the dispensing inlet, the sensor system including first and second sensors spaced apart along the dispensing channel such that the second sensor is located downstream of the first sensor. The method includes: forcing at least one article along a path through the dispensing passage; generating detection signals using the first and second sensors responsive to articles passing through the dispensing channel; and using the detection signals from the first and second sensors to monitor dispensing performance of the apparatus.

40 Claims, 11 Drawing Sheets

U.S. PATENT DOCUMENTS

| | | | |
|---|---|---|---|
| 3,730,388 A | 5/1973 | Bender | |
| 3,732,544 A | 5/1973 | Obland | |
| 3,780,907 A | 12/1973 | Colburn | |
| 3,815,780 A | 6/1974 | Bauer | |
| 3,837,139 A | 9/1974 | Roseberg | |
| 3,885,702 A | 5/1975 | Joslin | |
| 3,917,045 A | 11/1975 | Williams | |
| 4,223,751 A * | 9/1980 | Ayers et al. | 177/210 C |
| 4,267,942 A | 5/1981 | Wick | |
| 4,434,602 A | 3/1984 | Culpepper | |
| 4,471,428 A | 9/1984 | Dshkhunian et al. | |
| 4,546,901 A | 10/1985 | Buttarazzi | |
| 4,573,606 A | 3/1986 | Lewis | |
| 4,655,026 A | 4/1987 | Wigoda | |
| 4,664,289 A | 5/1987 | Shimizu | |
| 4,674,259 A | 6/1987 | Hills | |
| 4,674,651 A | 6/1987 | Scidmore | |
| 4,693,057 A | 9/1987 | Rittinger | |
| 4,695,954 A | 9/1987 | Rose | |
| 4,766,542 A | 8/1988 | Pilarczyk | |
| 4,767,023 A | 8/1988 | Hackmann | |
| 4,801,044 A | 1/1989 | Kubota et al. | |
| 4,805,377 A | 2/1989 | Carter | |
| 4,869,392 A | 9/1989 | Moulding, Jr. | |
| 4,918,604 A | 4/1990 | Baum | |
| 4,971,513 A | 11/1990 | Bergerioux | |
| 4,980,292 A | 12/1990 | Elbert | |
| 4,984,709 A | 1/1991 | Weinstein | |
| 5,018,644 A | 5/1991 | Hackmann | |
| 5,047,948 A | 9/1991 | Turner | |
| 5,317,645 A * | 5/1994 | Perozek et al. | 382/141 |
| 5,337,919 A | 8/1994 | Spaulding et al. | |
| 5,668,300 A | 9/1997 | Krökel et al. | |
| 5,768,327 A * | 6/1998 | Pinto et al. | 377/10 |
| 5,777,557 A | 7/1998 | Fayfield | |
| 5,808,296 A | 9/1998 | McMonagle et al. | |
| 5,884,806 A | 3/1999 | Boyer et al. | |
| 5,923,427 A | 7/1999 | Dong | |
| 6,006,946 A | 12/1999 | Williams et al. | |
| 6,036,812 A | 3/2000 | Williams et al. | |
| 6,176,392 B1 | 1/2001 | Williams et al. | |
| 6,211,784 B1 | 4/2001 | Nishide | |
| RE37,829 E | 9/2002 | Charhut | |
| 6,492,821 B1 | 12/2002 | Marko et al. | |
| 6,631,826 B2 * | 10/2003 | Pollard et al. | 221/156 |
| 6,736,286 B2 | 5/2004 | Hashimoto et al. | |
| 6,971,541 B2 | 12/2005 | Williams et al. | |
| 7,269,476 B2 * | 9/2007 | Ratnakar | 700/236 |
| 7,344,049 B2 * | 3/2008 | Daniels et al. | 221/92 |
| 2004/0004085 A1 * | 1/2004 | Williams et al. | 221/278 |
| 2006/0124656 A1 * | 6/2006 | Popovich, Jr. | 221/9 |
| 2006/0241807 A1 | 10/2006 | Daniels et al. | |

FOREIGN PATENT DOCUMENTS

| | | |
|---|---|---|
| GB | 1 168 758 | 10/1969 |
| GB | 1 411 951 | 10/1975 |
| JP | 51-000792 B | 1/1976 |
| JP | 52-047400 | 4/1977 |
| JP | 61-104904 | 5/1986 |
| JP | 63-208410 | 8/1988 |
| JP | 64-028102 | 1/1989 |
| JP | 1-288265 | 11/1989 |
| JP | 2-028417 | 1/1990 |

* cited by examiner

METHODS AND APPARATUS FOR DISPENSING SOLID PHARMACEUTICAL ARTICLES

RELATED APPLICATION(S)

The present application claims the benefit of U.S. Provisional Patent Application No. 60/938,835, filed May 18, 2007, the disclosure of which is hereby incorporated herein by reference in its entirety.

FIELD OF THE INVENTION

The present invention is directed generally to the dispensing of solid pharmaceutical articles and, more specifically, is directed to the automated dispensing of solid pharmaceutical articles.

BACKGROUND OF THE INVENTION

Pharmacy generally began with the compounding of medicines which entailed the actual mixing and preparing of medications. Heretofore, pharmacy has been, to a great extent, a profession of dispensing, that is, the pouring, counting, and labeling of a prescription, and subsequently transferring the dispensed medication to the patient. Because of the repetitiveness of many of the pharmacist's tasks, automation of these tasks has been desirable.

Some attempts have been made to automate the pharmacy environment. For example, U.S. Pat. No. 6,971,541 to Williams et al. describes an automated system for dispensing pharmaceuticals using dispensing bins. Each dispensing bin includes a hopper in which tablets are stored and a dispensing channel fluidly connecting the hopper to a dispensing outlet. Forward and reverse air flows are used to selectively convey the tablets through the dispensing channel in each of a dispensing direction (toward the outlet) and a reverse direction (toward the hopper). A counting sensor is positioned proximate the outlet of the dispensing channel and used to detect tablets passing the sensor in order to maintain a count of the tablets dispensed.

SUMMARY OF THE INVENTION

According to some embodiments of the present invention, a method is provided for dispensing solid pharmaceutical articles using an apparatus including a housing and a sensor system, the housing defining a dispensing passage having a dispensing inlet and a dispensing outlet downstream of the dispensing inlet, the sensor system including first and second sensors spaced apart along the dispensing channel such that the second sensor is located downstream of the first sensor. The method includes: forcing at least one article along a path through the dispensing passage; generating detection signals using the first and second sensors responsive to articles passing through the dispensing channel; and using the detection signals from the first and second sensors to monitor dispensing performance of the apparatus.

According to some embodiments of the present invention, an apparatus for dispensing solid pharmaceutical articles includes a housing, a drive mechanism and a sensor system. The housing defines a dispensing passage having a dispensing inlet and a dispensing outlet downstream of the dispensing inlet. The drive mechanism serves to force the articles along a path through the dispensing passage between the dispensing inlet and the dispensing outlet. The sensor system includes first and second sensors operative to detect articles passing through the dispensing passage and a controller to receive and use detection signals from the first and second sensors to monitor dispensing performance of the apparatus. The first and second sensors are spaced apart along the dispensing channel such that the second sensor is located downstream of the first sensor.

According to some embodiments of the present invention, a method is provided for dispensing solid pharmaceutical articles using an apparatus including a housing and a sensor system, the housing defining a dispensing channel having a dispensing inlet and a dispensing outlet downstream of the dispensing inlet, the sensor system including first and second sensors positioned along the dispensing channel. The method includes: forcing at least one article along a path through the dispensing channel; generating detection signals using the first and second sensors responsive to articles passing through the dispensing channel; and comparing the detection signals from the first and second sensors to determine whether a dispensing fault condition has occurred.

According to some embodiments of the present invention, a method is provided for dispensing solid pharmaceutical articles using an apparatus including a housing and a sensor system, the housing defining a dispensing channel having a dispensing inlet and a dispensing outlet downstream of the dispensing inlet, the sensor system including at least one sensor positioned along the dispensing channel. The method includes: forcing at least one article along a path through the dispensing channel; generating detection signals using the at least one sensor responsive to articles passing through the dispensing channel; and using a duration of at least one of the detection signals from the at least one sensor to determine whether a dispensing fault condition has occurred.

Further features, advantages and details of the present invention will be appreciated by those of ordinary skill in the art from a reading of the figures and the detailed description of the preferred embodiments that follow, such description being merely illustrative of the present invention.

DETAILED DESCRIPTION OF EMBODIMENTS OF THE INVENTION

Figure 1:
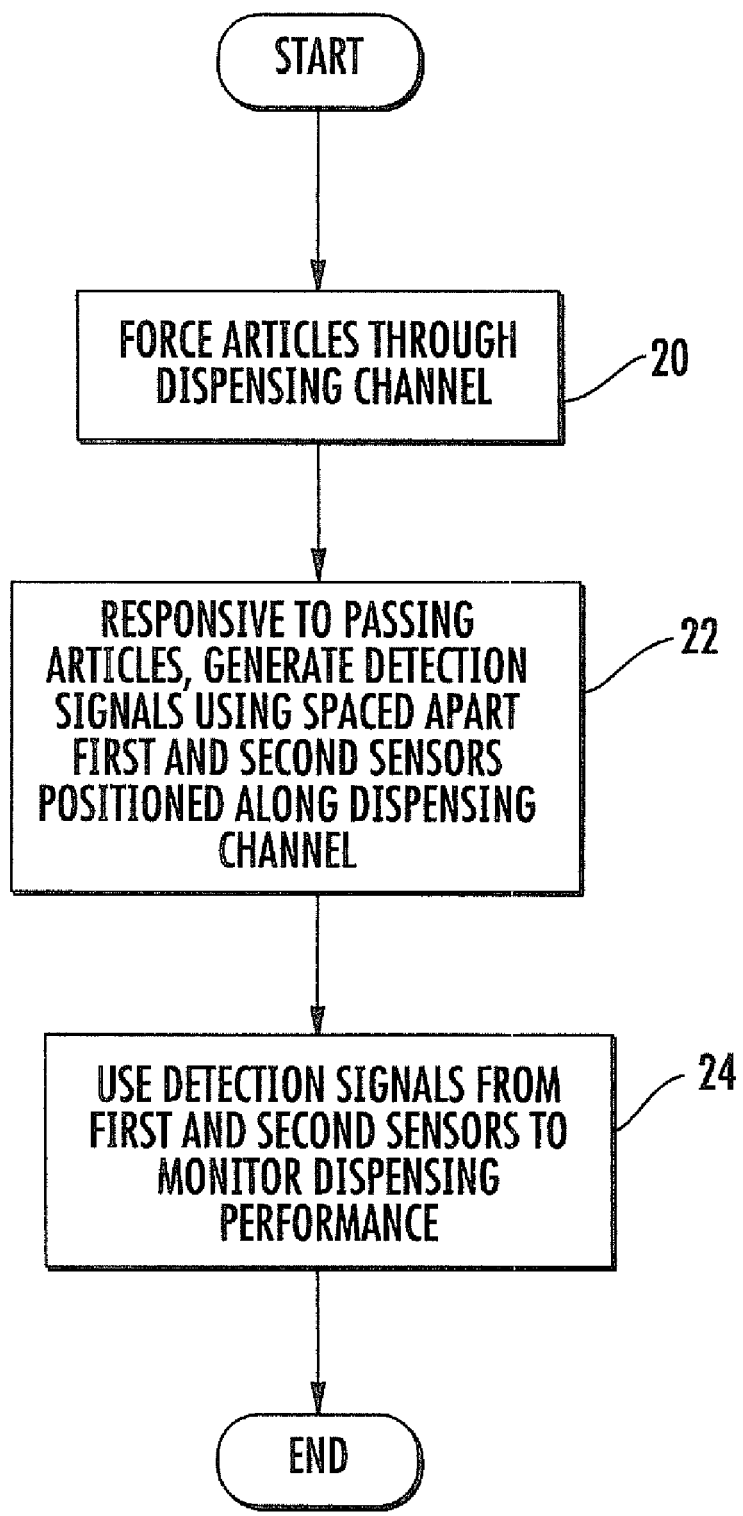
FIG. 1 is a flow chart illustrating methods according to embodiments of the present invention.

The present invention now will be described more fully hereinafter with reference to the accompanying drawings, in which illustrative embodiments of the invention are shown. In the drawings, the relative sizes of regions or features may be exaggerated for clarity. This invention may, however, be embodied in many different forms and should not be construed as limited to the embodiments set forth herein; rather, these embodiments are provided so that this disclosure will be thorough and complete, and will fully convey the scope of the invention to those skilled in the art.

It will be understood that when an element is referred to as being "coupled" or "connected" to another element, it can be directly coupled or connected to the other element or intervening elements may also be present. In contrast, when an element is referred to as being "directly coupled" or "directly connected" to another element, there are no intervening elements present. Like numbers refer to like elements throughout.

In addition, spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein the expression "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In accordance with embodiments of the present invention apparatus and methods are provided for dispensing solid pharmaceutical articles. In particular, such methods and apparatus may be used to dispense pharmaceuticals. With reference to FIG. 1, methods according to embodiments of the present invention may be executed using an apparatus including a housing, a flow generator, and a sensor system, the housing defining a dispensing channel having a dispensing inlet and a dispensing outlet downstream of the dispensing inlet, the sensor system including first and second sensors spaced apart along the dispensing channel such that the second sensor is located downstream of the first sensor. At least one drive gas flow is generated using the flow generator to force at least one article along a path through the dispensing channel (Block 20). The dispensing channel may or may not be fully enclosed. Responsive to articles passing through the dispensing channel, detection signals are generated using the first and second sensors (Block 22). The detection signals from the first and second sensors are used to monitor dispensing performance of the apparatus (Block 24). According to some embodiments, the articles are pharmaceutical tablets.

Figure 2:
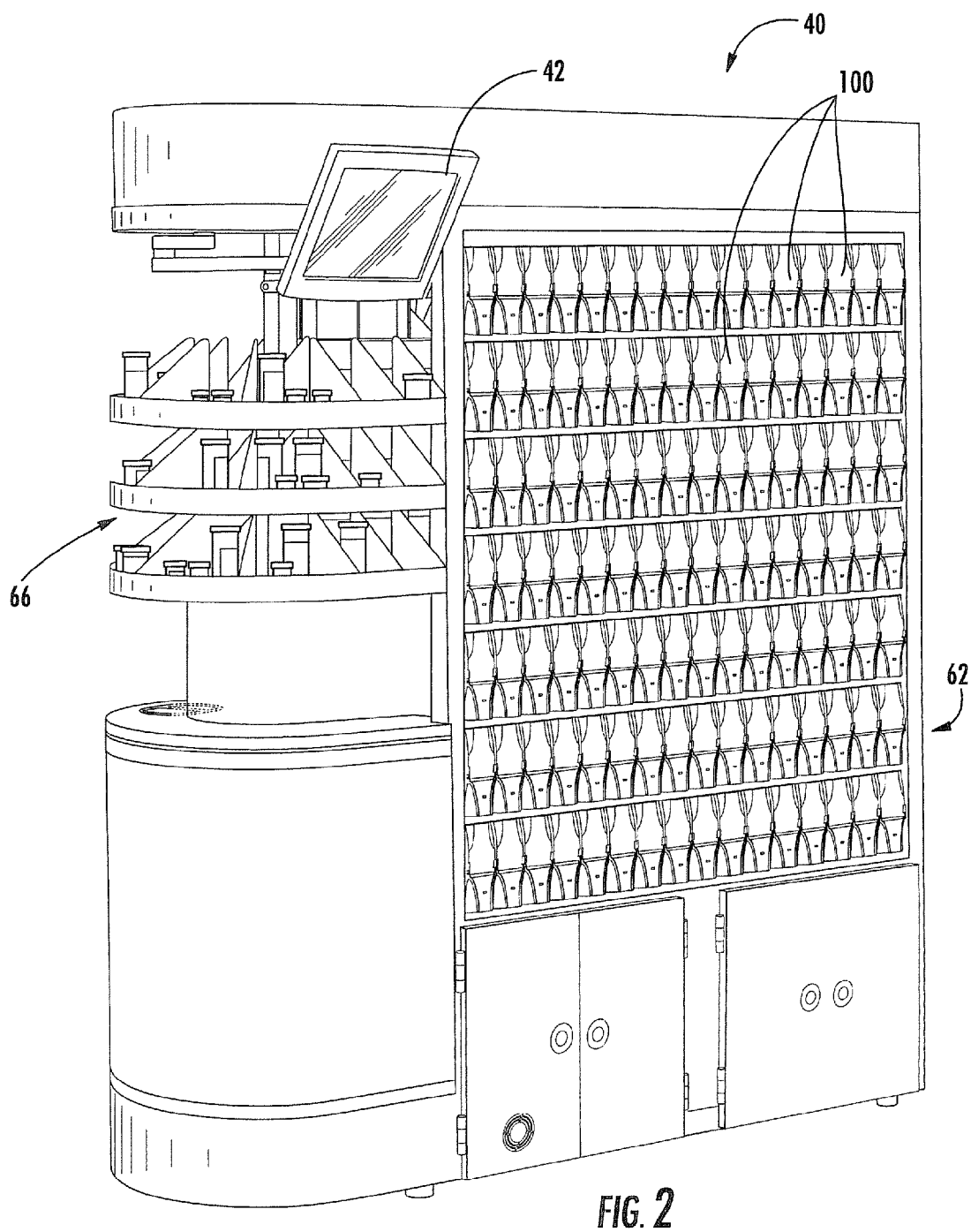
FIG. 2 is a perspective view of a pharmaceutical tablet dispensing system including a sensor system according to embodiments of the present invention.
Figure 3:
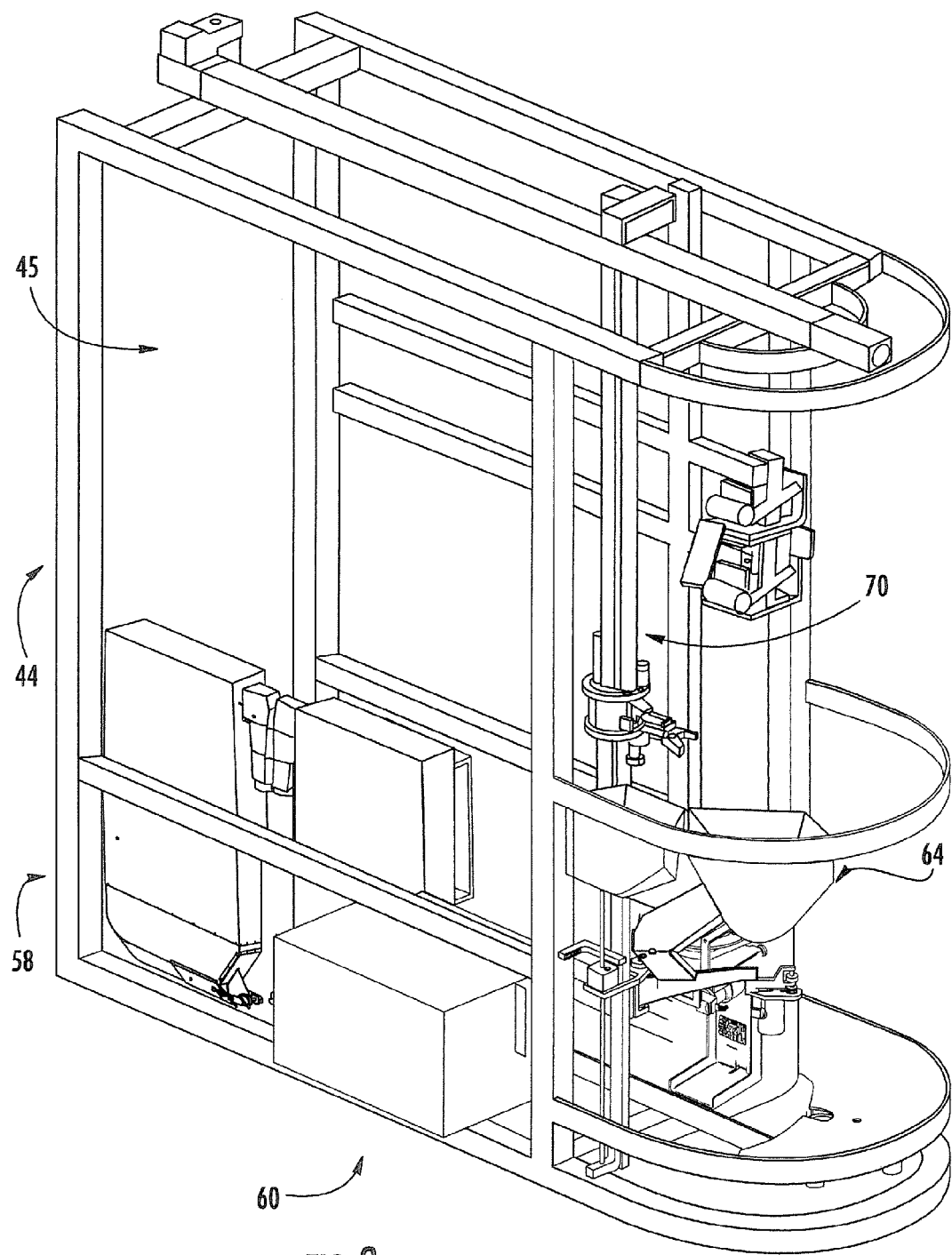
FIG. 3 is a cutaway view of the tablet dispensing system of FIG. 2 illustrating a container dispensing station, a labeling carrier, a dispensing carrier, and a closure dispensing station thereof.

A dispensing system according to embodiments of the present invention and that can carry out the foregoing methods is illustrated in FIGS. 2-8 and designated broadly therein at 40 (FIGS. 2 and 3). The dispensing system 40 includes a sensor system 102 (FIG. 8) according to embodiments of the present invention. The system 40 includes a support frame 44 for the mounting of its various components. Those skilled in this art will recognize that the frame 44 illustrated herein is exemplary and can take many configurations that would be suitable for use with the present invention. The frame 44 provides a strong, rigid foundation to which other components can be attached at desired locations, and other frame forms able to serve this purpose may also be acceptable for use with this invention.

The system 40 generally includes as operative stations a controller (represented herein by a graphical user interface 42), a container dispensing station 58, a labeling station 60, a tablet dispensing station 62, a closure dispensing station 64, and an offloading station 66. In the illustrated embodiment, containers, tablets and closures are moved between these stations with a dispensing carrier 70; however, in some embodiments, multiple carriers are employed. The dispensing carrier 70 has the capability of moving the container to designated locations within the cavity 45 of the frame 44. Except as discussed herein with regard to the dispensing station 62, each of the operative stations and the conveying devices may be of any suitable construction such as those described in detail in U.S. Pat. No. 6,971,541 to Williams et al. and/or U.S. Patent Publication No. US-2006-0241807-A1, the disclosures of which are hereby incorporated herein in their entireties.

The controller 42 controls the operation of the remainder of the system 40. In some embodiments, the controller 42 will be operatively connected with an external device, such as a personal or mainframe computer, that provides input information regarding prescriptions. In other embodiments, the controller 42 may be a stand-alone computer that directly receives manual input from a pharmacist or other operator. An exemplary controller is a conventional microprocessor-based personal computer.

In operation, the controller 42 signals the container dispensing station 58 that a container of a specified size is desired. In response, the container dispensing station 58 delivers a container for retrieval by the carrier 70. From the container dispensing station 58, the container is moved to the labeling station 60 by the carrier 70. The labeling station 60 includes a printer that is controlled by the controller 42. The printer prints and presents an adhesive label that is affixed to the container.

Figure 4:
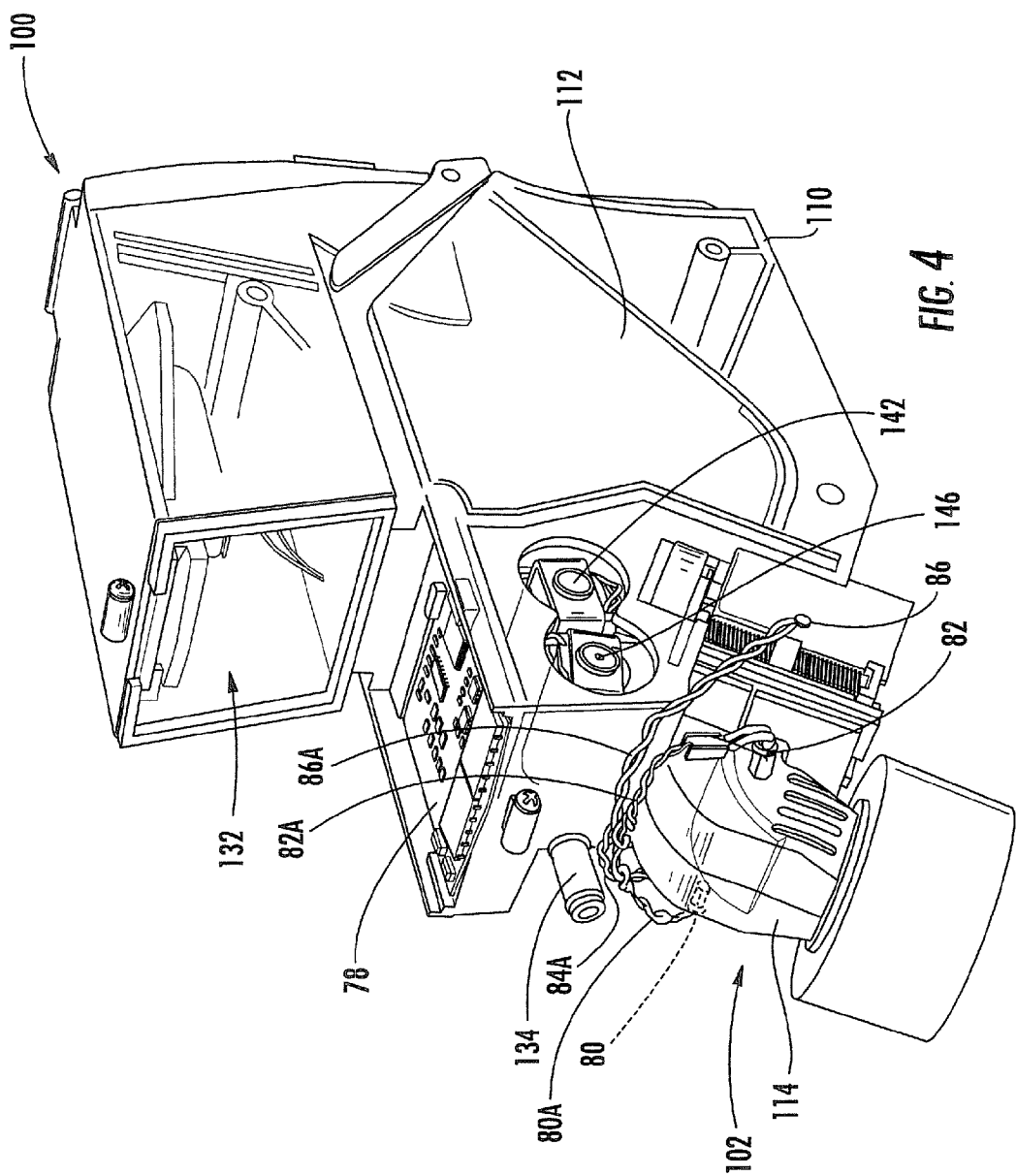
FIG. 4 is a front perspective view of a dispensing bin according to embodiments of the present invention.
Figure 5:
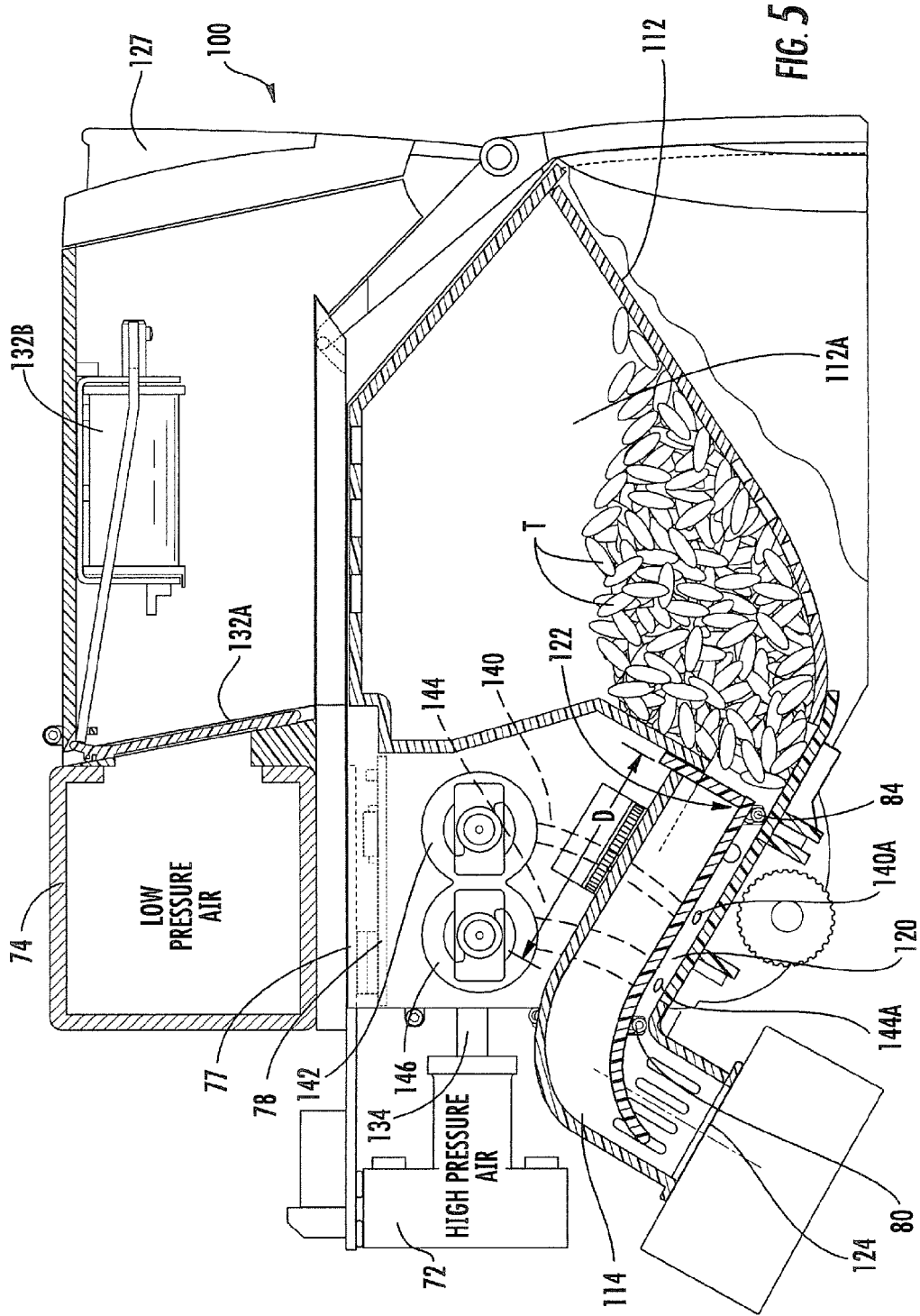
FIG. 5 is a cross-sectional view of the bin of FIG. 4 filled with tablets at rest.

Filling of labeled containers with tablets is carried out by the tablet dispensing station 62. The tablet dispensing station 62 comprises a plurality of tablet dispensing bin assemblies or bins 100 (described in more detail below), each of which holds a bulk supply of individual tablets (typically the bins 100 will hold different tablets). Referring to FIGS. 4 and 5, the dispensing bins 100, which may be substantially identical in size and configuration, are organized in an array mounted on the rails of the frame 44. Each dispensing bin 100 has a dispensing passage or channel 120 with an outlet 124 that faces generally in the same direction, to create an access region for the dispensing carrier 70. The identity of the tablets in each bin is known by the controller 42, which can direct the dispensing carrier 70 to transport the container to the proper bin 100 to fill the particular prescription. In some embodiments, the bins 100 may be labeled with a bar code or other indicia to allow the dispensing carrier 70 to confirm that it has arrived at the proper bin 100.

The dispensing bins 100 are configured to singulate, count, and dispense the tablets contained therein, with the operation of the bins 100 and the counting of the tablets being controlled by the controller 42. Some embodiments may employ the controller 42 as the device which monitors the locations and contents of the bins 100; others may employ the controller 42 to monitor the locations of the bins, with the bins 100 including indicia (such as a bar code or electronic transmitter) to identify the contents to the controller 42. In still other embodiments, the bins 100 may generate and provide location and content information to the controller 42, with the result that the bins 100 may be moved to different positions on the frame 42 without the need for manual modification of the controller 42 (i.e., the bins 100 will update the controller 42 automatically).

Any of a number of dispensing units that singulate and count discrete objects may be employed if suitably modified to include the inventive aspects disclosed herein. In particular, dispensing units that rely upon targeted air flow and a singulating nozzle assembly may be used, such as the devices described in U.S. Pat. No. 6,631,826 to Pollard et al. and/or U.S. Patent Publication No. US-2006-0241807-A1, each of which is hereby incorporated herein by reference in its entirety. Bins of this variety may also include additional features, such as those described below.

After the container is desirably filled by the tablet dispensing station 62, the dispensing carrier 70 moves the filled container to the closure dispensing station 64. The closure dispensing station 64 may house a bulk supply of closures and dispense and secure them onto a filled container. The dispensing carrier 70 then moves to the closed container, grasps it, and moves it to the offloading station 66.

Turning to the bins 100 in more detail, an exemplary bin 100 is shown in more detail in FIGS. 4-8. The bin 100 includes a housing 110 having a hopper portion 112 and a nozzle 114.

Figure 6:
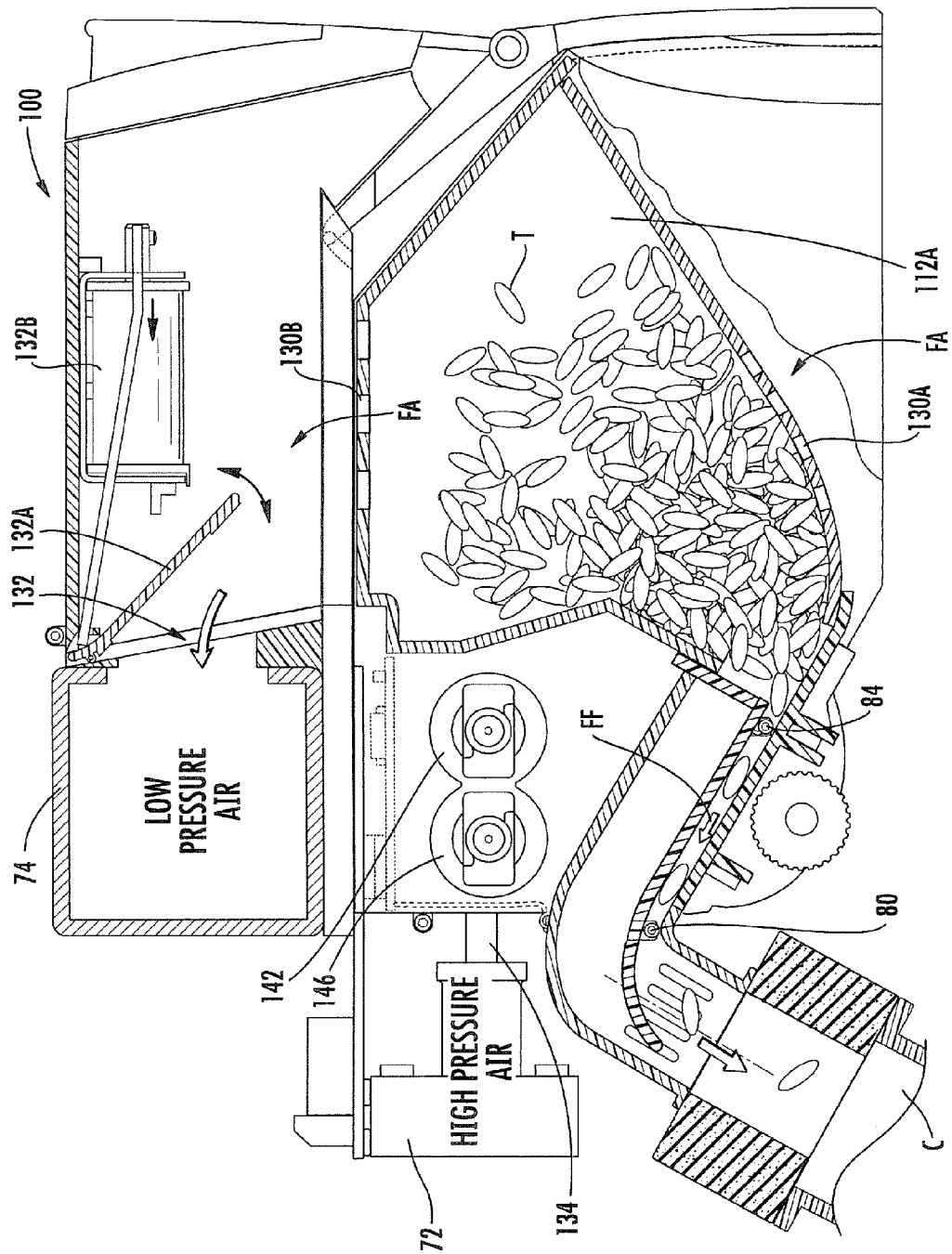
FIG. 6 is a cross-sectional view of the bin of FIG. 4 wherein tablets contained therein are being agitated and dispensed in a forward or dispensing direction.

Referring to FIG. 6, the hopper portion 112 defines a hopper chamber 112A that can be filled with tablets T. A lower screen 130A is provided in the floor of the hopper portion 112 and an upper screen 130B is provided in the ceiling of the hopper portion 112. As discussed below, air or other suitable gas can be flowed through the screens 130A, 130B and the chamber 112A to agitate the tablets T contained therein.

Figure 7:
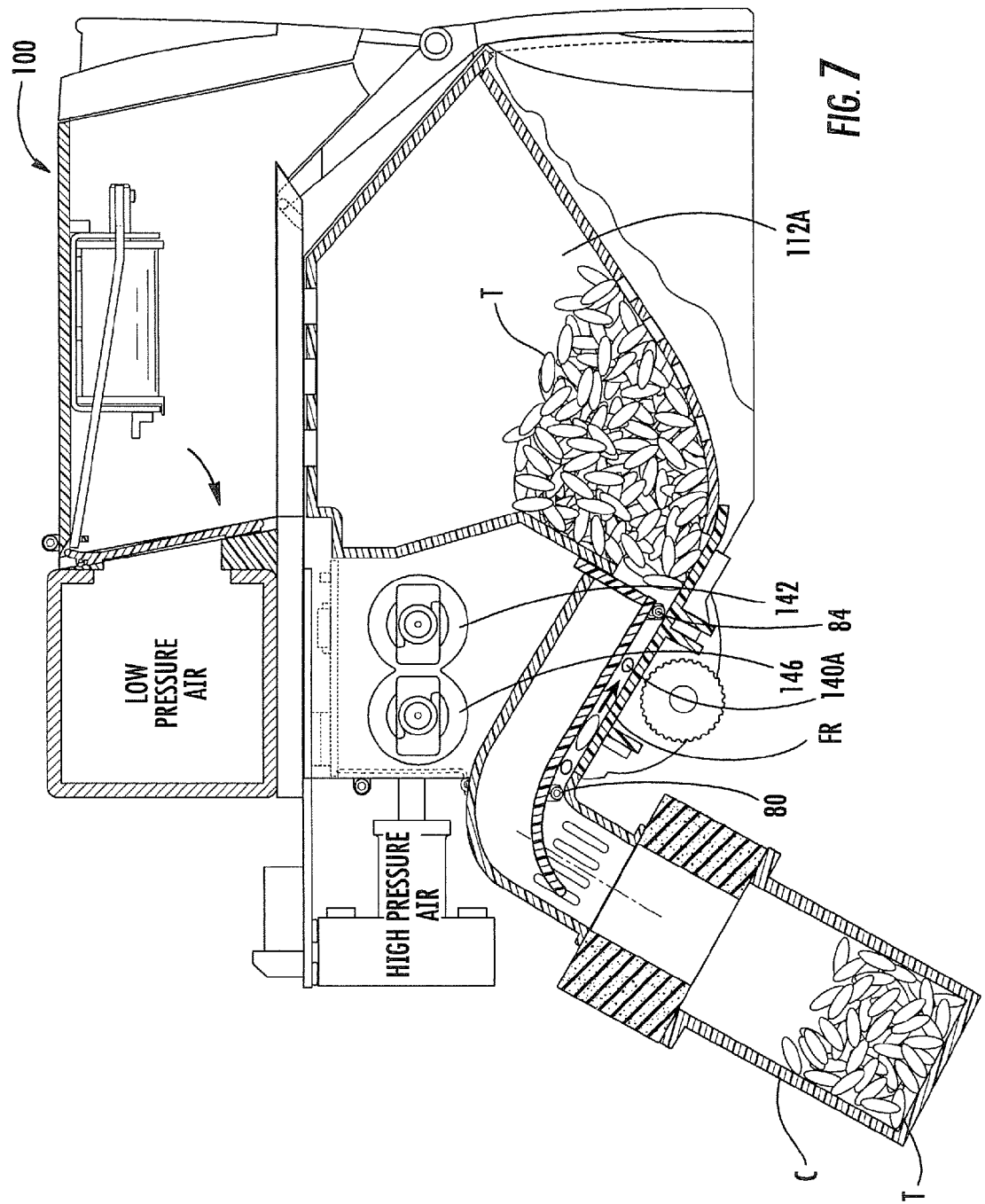
FIG. 7 is a cross-sectional view of the bin of FIG. 4 wherein a tablet is being returned to a hopper of the bin in a reverse direction.
Figure 8:
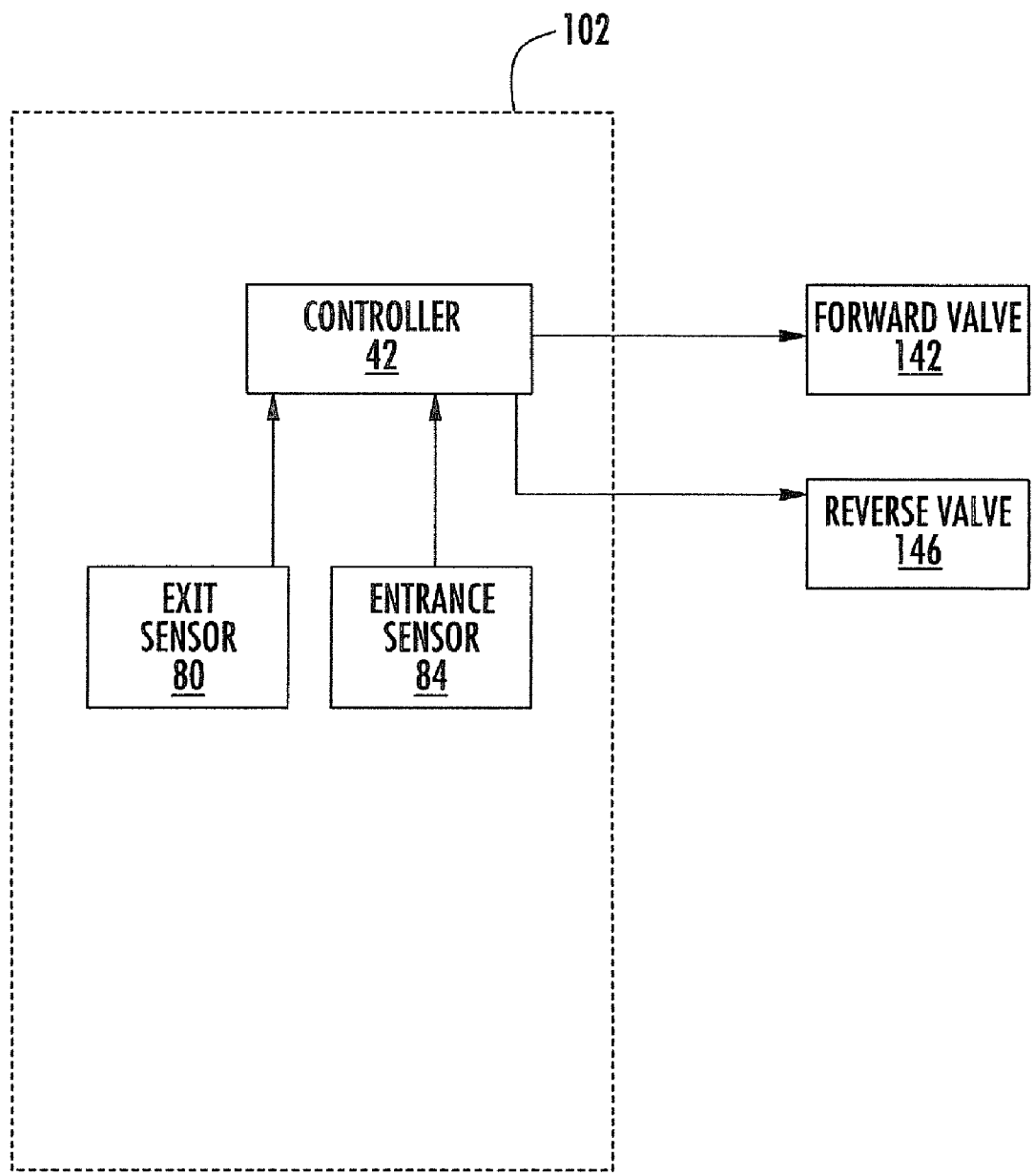
FIG. 8 is a block diagram representing a sensor system and control valves of the pharmaceutical dispensing system of FIG. 1.

With reference to FIG. 5, the nozzle 114 defines a dispensing channel 120 through which the tablets T can be dispensed one at a time. The dispensing channel 120 has an inlet 122 adjacent and fluidly connecting the channel 120 to the chamber 112A. The dispensing channel 120 has an outlet 124 downstream from and opposite the inlet 122 and through which tablets may exit the nozzle 114 to be dispensed into the container C (FIG. 7).

The housing 110 further includes a low pressure port 132 and a high pressure nozzle 134 (FIGS. 4 and 6). A door 132A is provided to selectively open and close the port 132 by operation of an associated solenoid 132B.

With continued reference to FIG. 5, a forward jet passage 140 is fluidly connected to the high pressure nozzle 134 and terminates in a forward jet aperture 140A at the dispensing channel 120. A forward control valve 142 is operable to control airflow to the jet aperture 140A. A rearward or reverse jet passage 144 is also fluidly connected to the high pressure nozzle 134 and terminates in a rearward or reverse jet aperture 144A at the dispensing channel 120. A reverse control valve 146 is operable to control airflow to the jet aperture 144A.

According to some embodiments and as described in U.S. Patent Publication No. US-2006-0241807-A1, the tablet dispensing station 62 includes a low pressure manifold 74 fluidly connected to a low pressure source such as a vacuum motor (not shown), which provides low level (i.e., about 2 psi) suction to draw air FA through (in succession) the screen 130A, the chamber 112A, the screen 130B and the port 132 to agitate tablets within the hopper chamber 112A (FIG. 6). Also, a high pressure (i.e., about 30 psi) conduit 72 fluidly connected to a high pressure source (not shown) is fluidly connected to the high pressure nozzle 134 to supply high pressure air to the jet apertures 140A, 144A. Further, a connector circuit board 77 is mounted horizontally below the manifold 74. The circuit board 77 or other electrical connector provides an electrical connection between the controller 42 and a bin-controlling circuit board 78 (or other electronic component) of the bin 100 for power and data signals to/from the controller 42.

The sensor system 102 includes a front or exit sensor 80 and a rear or entrance sensor 84 positioned along the channel 120. The exit sensor 80 is located downstream (i.e., in the forward or dispensing direction of the tablet flow path through the dispensing channel 120) from the entrance sensor 84 along the dispensing channel 120. The exit sensor 80 is mounted in the nozzle 114 proximate the outlet 124 and distal from the inlet 122 and faces the channel 120. The entrance sensor 84 is mounted in the nozzle 114 proximate the inlet 122 and distal from the outlet 124 and also faces the channel 120. The sensors 80, 84 are tablet detecting sensors and are operably connected to associated sensor receiver/processor electronics. The sensors 80, 84 may be electrically connected to an associated controller by lead wires 80A, 84A. According to some embodiments, the associated controller is or includes the controller 42 and/or the circuit board 78. As further discussed below, the sensors 80, 84 are configured and positioned to detect the tablets T as they pass through the dispensing channel 120. The sensors 80, 84 and the associated controller 42 together comprise a sensor system 102 operative to monitor flow of tablets T through the channel 120 and, thereby, dispensing performance of the bin 100. According to some embodiments, the controller 42 uses detection signals from at least one of the sensors 80, 84 to count the dispensed tablets. According to some embodiments, at least the exit sensor 80 is used for this purpose. In some cases, the sensor system operates the valves 142, 146 or other devices in response to identified or determined conditions or performance in dispensing. While two sensors 80, 84 are described herein, apparatus and methods according to embodiments of the present invention may use sensor systems that use more than two tablet detection sensors along the flow path.

According to some embodiments, the sensors 80, 84 are photoelectric sensors. According to some embodiments, the sensors 80, 84 are infrared (IR) sensors. According to some embodiments, photoemitters 82 and 86 (e.g., IR emitters) are mounted in the nozzle opposite the sensors 80 and 84, respectively, to emit photoemissions toward the respective sensors 80, 84 across the channel 120. The photoemitters 82, 86 may be operatively connected to the controller 42 or circuit board 78 by wires 82A, 86A. According to some embodiments, all or some of the components 80, 84 and 82, 86 may include both a photoemitter and a photodetector, whereby the components 82, 86 may also serve as sensors. For the purpose of explanation, the illustrated embodiment will be described with only the components 80, 84 being sensors (i.e., the sensors 80, 84 receive photoemissions from the photoemitters 82, 86). Other types of sensors may be employed as well. Other suitable types of sensors may include, for example, UV, RF, capacitive and EMF sensors.

The exit sensor 80 and the entrance sensor 84 are spaced apart along the channel 120 a distance D (FIG. 5). The preferred or minimum distance D may be determined by the type of sensor and/or other parameters or arrangements or physical limitations of the components. According to some embodiments, the distance D should be large enough to prevent cross-talk between the components and to provide two distinct signals from the respective sensors 80, 84. The minimum distance D may also be limited or determined by the time needed to prevent an extra pill from exiting the channel 120 (i.e., once the requested count is reached, the distance D should allow enough time to stop an extra pill from exiting).

According to some embodiments, the entrance sensor 84 is positioned along the channel 120 at, in or immediately adjacent the inlet 122. According to some embodiments, the exit sensor 80 is positioned along the channel 120 at, in or immediately adjacent the outlet 124.

Exemplary operation of the dispensing system 40 will now be described. The bin 100 is filled with tablets T to be dispensed. The tablets T may initially be at rest as shown in FIG. 5. At this time, the valves 142, 146 are closed so that no gas flow is provided through the jet outlets 140A, 144A.

To fill the container C, the dispensing carrier 70, directed by the controller 42, moves the container C to the exit port of the selected dispensing bin 100. The controller 42 signals the solenoid 132B to open the door 132A. This opening of the door 132A draws low pressure air up through the hopper chamber 112A to the manifold 74, thereby agitating the tablets T contained in the hopper chamber 112B.

Once agitation has commenced, the controller 42 signals the forward valve 142 to open (while the reverse valve 146 remains closed). The opened valve 142 permits the pressurized gas from the gas source 72 to flow through the passage 140 and out through the forward drive jet outlet 140A. The pressurized flow from the jet outlet 140A creates a high velocity gas jet that generates suction that causes a forward flow FF of high pressure, high velocity air to be drawn outwardly through the dispensing channel 120 in a dispensing direction (FIG. 6). Tablets T are oriented into a preferred orientation by the shape of the inlet 122 to the dispensing channel 120 and dispensed into the container C through the dispensing channel 120 and the outlet 124 under the force of the forward flow FF.

Once dispensing is complete (i.e., a predetermined number of tablets have been counted by the controller 42 as dispensed), the controller 42 activates the forward valve 142 to close and the reverse valve 146 to open. The opened valve 146 permits the pressurized gas from the gas source 72 to flow through the passage 144 and out through the reverse drive jet outlet 144A. The pressurized flow from the jet outlet 144A creates a high velocity gas jet that generates suction that causes a reverse (i.e., rearward) flow FR of high pressure air to be drawn inwardly through the dispensing channel 120 toward the chamber 112A in a reverse or return direction. In this manner, the airflow is reversed and any tablets T remaining in the channel 120 are returned to the chamber 112A under the force of the reverse flow (FIG. 7).

While, in the foregoing description, the controller 42 controls the valves 142, 146, the valves 142, 146 may alternatively be controlled by a local controller unique to each bin 100. The bin 100 can be filled or replenished with tablets via access from a pivoting door 127 (FIG. 5) located at the upper rear portion of the bin 100, for example. As disclosed in U.S. Patent Publication No. US-2006-0241807-A1, the bin 100 may include components that permit the entry to the dispensing channel 120 to be adjusted in size to complement the size and configuration of the tablet to be dispensed.

During the dispensing phase (i.e., when the forward flow FF is being generated), a tablet jam may occur. A tablet jam is a condition wherein one or more tablets are caught up in the bin 100 such that tablets T will not feed into or through the dispensing channel 120 under the force of the forward flow FF. A jam is indicated if the entrance sensor 84 has not detected a pill within a specified time period (e.g., one second). When a tablet jam is identified by the controller 42, the controller 42 will close the forward valve 142 and open the reverse valve 146 to generate the reverse flow FR to clear a perceived tablet jam. This action of the controller 42 may be referred to as issuing a "jam clear".

According to some embodiments, the controller 42 will execute a calibration procedure between dispensing sessions (i.e., between the end of a forward flow FF and the initiation of the next forward flow FF) in order to calibrate the sensors 80, 84. According to some embodiments, the calibration procedure includes opening the reverse valve 146 to generate the reverse flow FR while calibrating the sensors 80, 84. This may ensure that no tablets or tablet fragments occlude the sensors 80, 84 and thereby corrupt the calibration. The controller 42 may conduct the calibration procedure automatically and/or shortly or immediately after a dispensing session and the bin 100 may remain idle (i.e., with neither a forward flow FF nor a reverse flow FR being generated) during an idle period between the end of the calibration reverse flow FR and the initiation of the next dispensing session.

Typically, an operator will request that a desired number of tablets be dispensed ("the requested count"). The sensors 80, 84 detect the tablets T as they pass through predetermined points in the dispensing channel 120, as discussed in more detail below. The controller 42 uses the detection signals from the sensors 80, 84 to monitor and maintain a registered count of the tablets T dispensed ("the system count"). When the system count matches the requested count, the controller 42 will deem the dispensing complete and cease dispensing of the tablets T. If the controller miscounts the tablets actually dispensed, there may be a mismatch between the requested count and the final actual count.

In practice and in the absence of the apparatus and methods of the present invention, the foregoing processes may suffer from various fault conditions or other dispensing concerns. In prior art systems of the type employing only a single counting sensor or set of counting sensors at one location along the dispensing channel (e.g., at the exit end) to detect tablets in the dispensing channel (hereinafter referred to as "prior art single sensor systems"), these fault conditions may result in inaccurate counts such as counting a tablet that is not dispensed, failing to count a tablet that is dispensed, or failing to recognize a partial tablet.

The foregoing concerns may be addressed by the sensor system 102 of the bin 100 and methods in accordance with embodiments of the present invention. According to some embodiments, the entrance sensor 84 proximate the inlet 122 of the channel 120 performs the duty of detecting tablet jams and the exit sensor 80 proximate the exit or outlet 124 performs the duty of counting the dispensed tablets. By separating these two functions, the exit sensor 80 (i.e., the count sensor) can be guarded by the entrance sensor 84 (i.e., the jam sensor) to ensure that no tablets are in the dispensing channel 120 during a jam clear. The two sensors 80, 84 can also be cooperatively employed to detect and identify other modes of failure.

Such failure modes are called "exception events" and arise when the sensor output does not follow the expected pulse width and travel times for a singulated pill in standard operation of the bin 100. Some exception events and corresponding operations of the bin 100 that may be encountered will be described hereinbelow. However, it will be appreciated that this description is not exhaustive of the advantageous uses of the apparatus in accordance with embodiments of the present invention.

In some cases, two or more tablets T may be disposed or "preloaded" in the channel 120 in or closely adjacent the inlet 122 prior to actuation of the forward valve 142 to generate the forward flow FF. This condition may be referred to as a "preload dispensing fault condition". A preload dispensing fault condition may occur when tablets in the dispensing channel 120 are not fully returned to the hopper chamber 112A by a reverse flow or "jam clear" intended to clear the dispensing channel 120, for example. A preload dispensing fault condition may also occur when tablets unintentionally migrate into the dispensing channel 120 from the hopper. For example, during the idle period between a jam clear or other reverse flow FR and the initiation of the next forward flow FF, tablets may slide or vibrate out of the hopper chamber 112A and into the inlet 122 or the dispensing channel 120. In prior art single sensor systems, upon initiation of the forward flow FF, the two or more preloaded tablets may travel down the channel 120 in contact with or very closely adjacent one another so that the two or more tablets pass the counting sensor (which is typically located proximate the dispensing outlet) together. The counting sensor may generate only a single, extra long detection pulse for the two or more tablets rather than two or more discrete pulses that are required to register a count of two or more tablets. As a result, two or more tablets are dispensed through the dispensing outlet but the system count of dispensed tablets is only incremented by one tablet.

In accordance with embodiments of the present invention, a preload dispensing fault condition can be identified and corrected by monitoring the entrance sensor 84. More particularly, the entrance sensor 84 is configured and located with respect to the dispensing channel 120 and the inlet 122 such that, in the case of a preload dispensing fault condition, one or more of the tablets will occlude the entrance sensor 84. When this condition occurs prior to initiation of the forward flow FF, the entrance sensor 84 will provide a detection signal to the controller 42 indicating that the one or more tablets is/are at the entrance sensor 84. In response to the detection signal from the entrance sensor 84 prior to initiating the forward flow FF, the controller 42 identifies the existence of the preload dispensing fault condition. Further in response, the controller 42 will thereafter open the reverse valve 146 to generate the reverse flow FR to force any tablets T lingering in the channel 120 back into the hopper chamber 112A. In this manner, the channel 120 is cleared and the preload dispensing fault condition is removed prior to the onset of tablet dispensing.

A preload dispensing fault may also occur wherein the preloaded tablet or tablets are disposed in the dispensing channel 120 between the entrance sensor 84 and the exit sensor 80 prior to actuation of the forward valve 142 to generate the forward flow FF. The preloaded tablets may not occlude the entrance sensor 84. According to some embodiments of the present invention, preload dispensing fault conditions of this type are identified and corrected by continuously monitoring the entrance sensor 84 even when the bin 100 is idle. According to some embodiments, the entrance sensor 84 is continuously monitored at least from the end of the actuation of the reverse flow FR during calibration as discussed above to the start of the forward flow FF to begin a dispensing session (i.e., the idle period). According to some embodiments, the entrance sensor 84 is also continuously monitored throughout the calibration period. According to some embodiments, the entrance sensor 84 is continuously monitored at all times. If a tablet is detected by the entrance sensor 84 during the idle period, the controller 42 identifies the existence of a preload dispensing fault condition. The controller 42 may respond to the identified fault condition by generating the reverse flow FR to force any tablets lingering in the channel 120 back into the hopper chamber 112A. In this manner, the channel 120 is cleared and the preload dispensing fault condition is removed prior to the onset of tablet dispensing.

Figure 9:
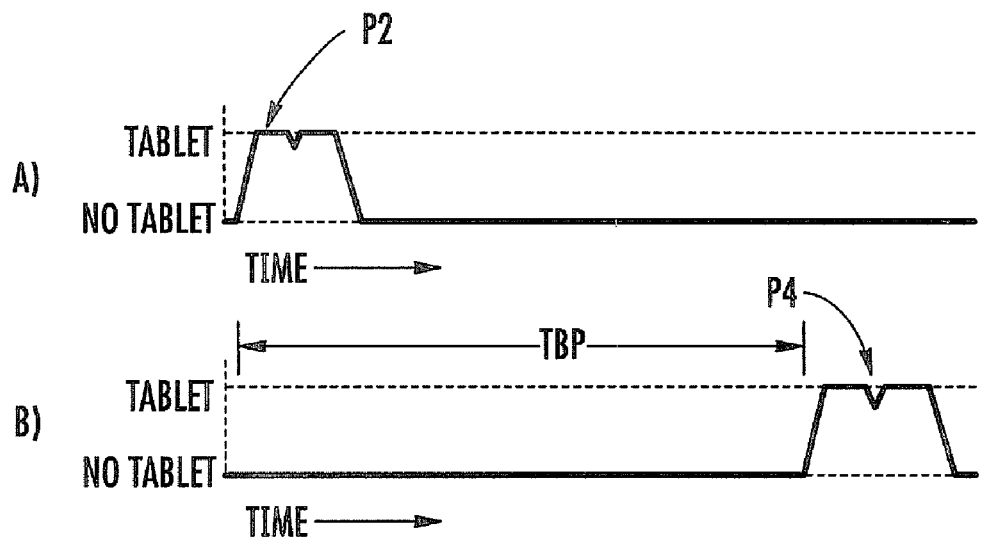
FIGS. 9-13 are schematic diagrams representing detection pulse signals of an entrance sensor and an exit sensor of the sensor system of FIG. 8 over time.

The sensor system 102 may employ the following method to address a "tandem dispensing fault condition." With reference to FIG. 9, when a tandem dispensing fault condition is present, the controller 42 may generate the forward flow FF to dispense the tablets as discussed above with regard to the prior art single sensor systems. This may occur if the entrance sensor 84 is not relied upon to sense preloaded tablets or the tandem condition is not detectable because the configuration/locations of the tablets do not cause the sensor 84 to immediately start with a tablet detection. The outputs of the sensors 80, 84 are monitored by the controller 42 and compared. Each of the two tablets passes the entrance sensor 84 in immediate succession, which causes the entrance sensor to generate a single pulse P2 as represented by the signal pulse graph A) of FIG. 9. The signal pulse P2 has a duration that is larger than that of a prescribed or average reference duration for a single tablet passing the sensor 84 during dispensing. Thereafter, the two tablets pass the exit sensor 80 in immediate succession, which causes the exit sensor 80 to generate one continuous, long duration signal pulse P4 as represented by the detector pulse graph B) of FIG. 9. The signal pulse P4 has a duration that is larger than that of a prescribed or average reference duration for a single tablet passing the sensor 80 during dispensing. The controller 42 compares the durations of the signals P2, P4 with the corresponding expected or average signal pulse durations and also compares the time TBP between the pulses P2, P4 with the expected or average time between pulses for standard operation, and determines that a tandem dispensing fault condition has occurred. In response, the controller 42 may increment the system dispensed count by an appropriate amount and/or alert an operator. The expected or average signal pulse durations for the sensors 80, 84 and the expected or average time between the pulses of the sensors 80, 84 may be determined using average entrance, exit and nozzle velocities determined as described below.

In some cases, a first tablet T lingers in the dispensing channel 120 during dispensing so that a second tablet T catches up to and collides with the first tablet before the first tablet is detected or completely detected by a counting sensor. The second tablet travels down the channel 120 in contact with the first tablet so that the first and second tablets pass the counting sensor together, responsive to which the counting sensor generates a single, extended duration signal pulse. This condition may be referred to as a "collision dispensing fault condition". In prior art single sensor systems, the single, extended duration signal pulse may simply be counted as a single tablet. As a result, two tablets are actually dispensed from the outlet but the system tablet dispense count is only incremented by one tablet.

Figure 10:
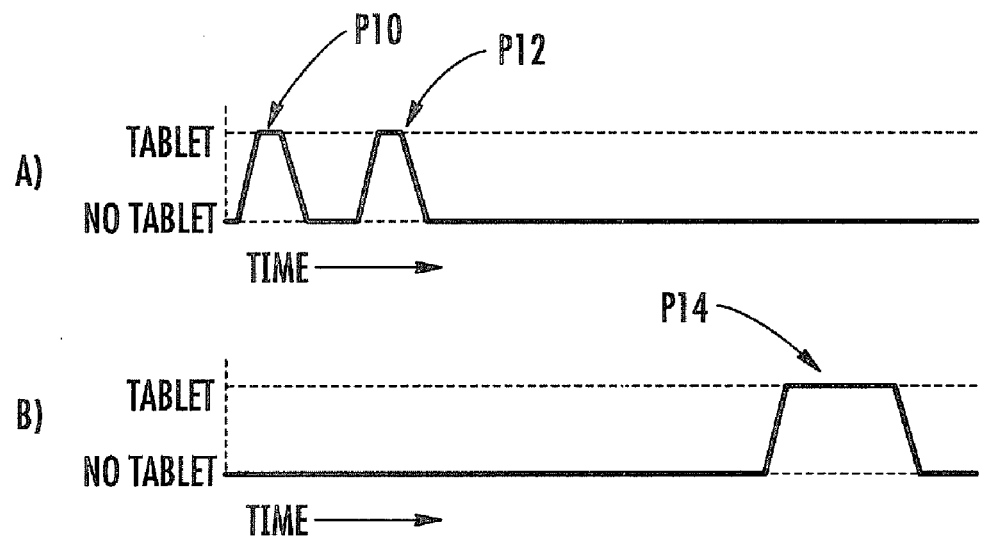

In accordance with embodiments of the present invention, a collision dispensing fault condition can be identified and corrected by monitoring the exit sensor 80 and the entrance sensor 84. More particularly, the outputs of the exit sensor 80 and the entrance sensor 84 are monitored by the controller 42 and compared. In the case of a collision dispensing fault condition, each of the two tablets passes the entrance sensor 84 in turn and with spacing between the tablets, which causes the entrance sensor 84 to generate two discrete signal pulses P10, P12 in sequence over time, as represented by the signal pulse graph A) of FIG. 10. These two pulses P10, P12 have a duration corresponding to a typical single tablet. Thereafter, the two tablets pass the exit sensor 80 in immediate succession, which causes the exit sensor 80 to generate one long duration signal pulse P14 as represented by the detector pulse graph B) of FIG. 10. The controller 42 compares the signals P10, P12, P14 from the sensors 80, 84 and determines that a collision dispensing fault condition has occurred. In response, the controller 42 may increment the system dispensed count total by the appropriate amount (in this example, two). Alternatively, in response, the controller 42 may issue an alert to an operator or the like indicating that a tablet may have been dispensed but not counted.

In some cases in prior art single sensor systems, a tablet that has been previously detected by a count sensor and counted by the sensor as dispensed is drawn back into or through the dispensing channel by a reverse drive gas flow FR (i.e., the tablet is aspirated back into the dispensing channel or hopper chamber). This occurrence may be referred to as an "aspiration dispensing fault condition". In prior art single sensor systems, the system count will exceed the actual number of dispensed tablets.

Figure 11:
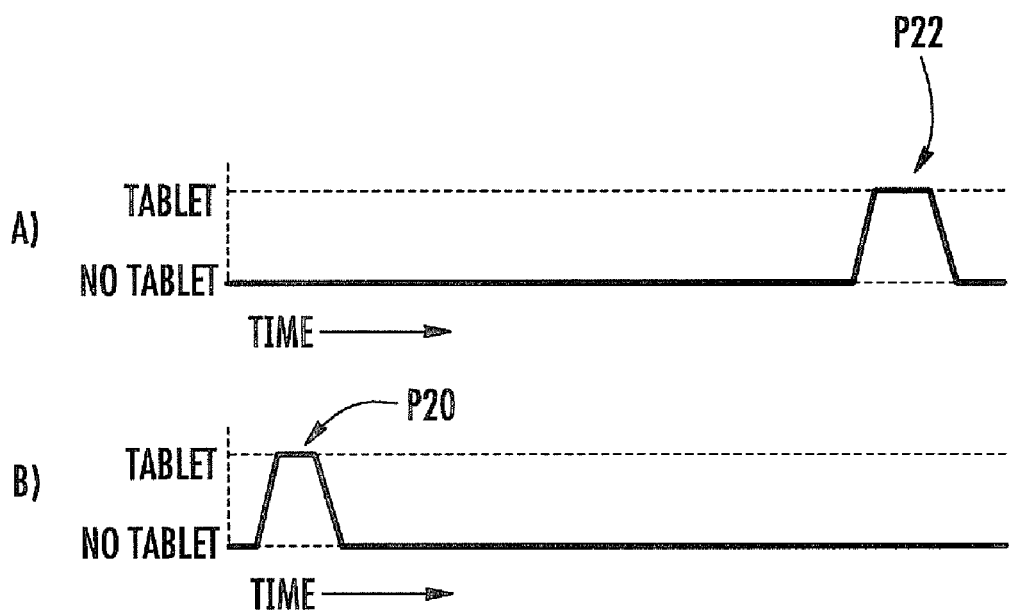

In accordance with embodiments of the present invention, an aspiration dispensing fault condition can be identified and corrected by monitoring the exit sensor 80 and the entrance sensor 84, and the direction of drive gas flow. More particularly, the outputs of the exit sensor 80 and the entrance sensor 84 are monitored by the controller 42 and compared. Each signal pulse from the exit sensor 80 will be accounted for if preceded by a corresponding signal pulse from the entrance sensor 84. Under normal (nonfault) conditions, each tablet drawn from the hopper 112A passes the entrance sensor 84 and then the exit sensor 80 and generates corresponding signal pulses in sequence. In the case of an aspiration dispensing fault condition, a tablet previously counted as dispensed passes the exit sensor 80, which causes the exit sensor 80 to generate a signal pulse P20 as represented by the detector pulse graph B) of FIG. 11. Thereafter, the tablet passes the entrance sensor 84, which causes the entrance sensor 84 to generate a signal pulse P22 as represented by the detector pulse graph A) of FIG. 11. The controller 42 determines that the drive gas flow was in the reverse direction when the pulses P20, P22 were generated and compares the signals P20, P22 from the sensors 80, 84. The controller determines that the exit signal pulse P20 did not have a corresponding preceding entrance sensor pulse and the exit sensor detection pulse P20 was triggered or generated prior to the entrance sensor detection pulse P22. From this, the controller 42 determines that an aspiration dispensing fault condition has occurred. In response, the controller 42 may decrement the system dispensing count total by one. Alternatively, in response, the controller 42 may issue an alert to an operator indicating that a tablet may have been counted and thereafter aspirated.

In some cases in prior art single sensor systems, jams are detected using the single sensor, which is typically positioned proximate the outlet of the dispensing channel. If, when the forward drive gas flow is being generated, some prescribed length of time (e.g., 1.0 second) passes without a tablet being detected by the single sensor, the system will issue a reverse drive gas flow in order to clear an upstream jam in the dispensing channel (i.e., the presumed cause of the failure to detect a tablet at the sensor). However, because of the length of time required for a tablet to travel from the entrance, the reverse drive gas jet flow may be initiated while a tablet is in fact en route to the exit count sensor such that the tablet occludes the count sensor, reverses direction in the dispensing channel, and returns back to the hopper chamber. This occurrence may be referred to as a "tablet reversal dispensing fault condition". In prior art single sensor systems, the tablet may be counted as dispensed and the reversal may not be registered so that the system count is increased over the actual number of tablets dispensed by one. Moreover, in some cases, the reversed tablet may be counted twice (once when passing the count sensor in the dispensing direction and once when passing the count sensor in the reverse direction).

In accordance with embodiments of the present invention, a tablet reversal dispensing fault condition is prevented by triggering the reverse drive gas flow (jam clear) off of the entrance sensor 84 instead of the counting sensor 80. More particularly, the controller 42 monitors the entrance sensor 84. If a tablet is not detected by the entrance sensor 84 within a prescribed length of time (wait time) while the forward drive gas flow (i.e., the dispensing flow) is being generated, the controller 42 will identify a tablet jam condition. Responsive to the tablet jam condition, the controller 42 will issue a jam clear (i.e., open the reverse valve 146 to generate a burst or sustained reverse flow FR). In this manner, the entrance sensor 84 "guards" the exit sensor 80.

Figure 12:
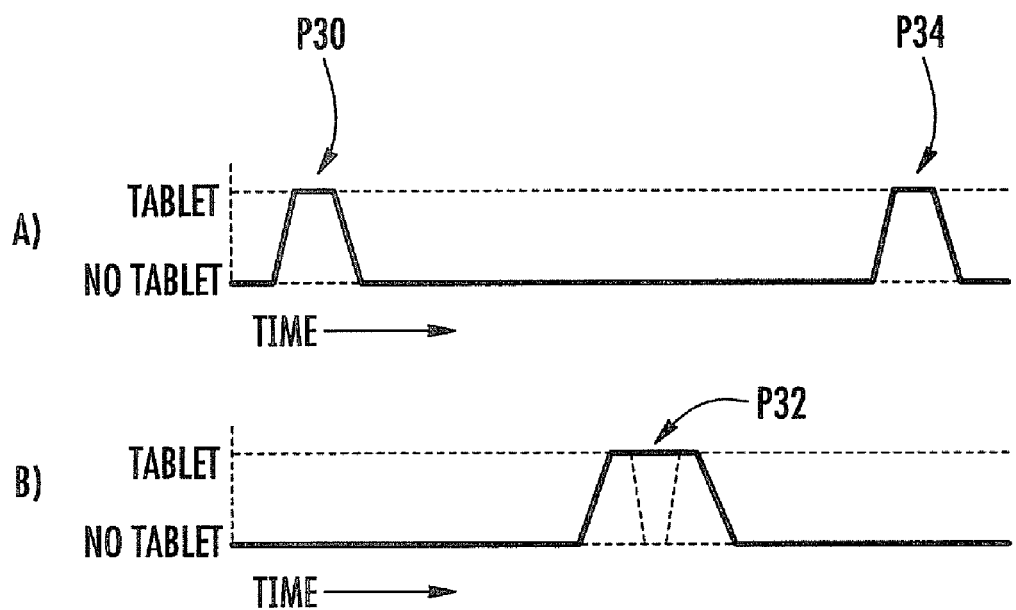

The sensor system 102 may additionally or alternatively employ the following method to identify and correct a tablet reversal dispensing fault condition by monitoring the exit sensor 80, the entrance sensor 84, and the direction of drive gas flow. The outputs of the exit sensor 80 and the entrance sensor 84 are monitored by the controller 42 and compared. In the case of a tablet reversal dispensing fault condition, a tablet passes the entrance sensor 84 (which causes the entrance sensor 84 to generate a typical duration signal pulse P30 as represented by the detector pulse graph A) of FIG. 12), thereafter passes the exit sensor 80 (which causes the exit sensor 80 to generate an extra long duration signal pulse (or two signal pulses as shown by the dotted line) P32 as represented by the detector pulse graph B) of FIG. 12), and thereafter again passes the entrance sensor 84 (which causes the entrance sensor 84 to generate a typical duration signal pulse P34). The controller 42 determines that the drive gas flow was in the forward direction during the pulse P30 and in the reverse direction during the pulse P34, compares the signals P30, P32, P34 from the sensors 80, 84, and determines that a tablet reversal dispensing fault condition has occurred. In response, the controller 42 may decrement the dispensing count total by one. Alternatively, in response, the controller 42 may issue an alert to an operator indicating that a tablet may have been counted and thereafter reversed.

While events such as those described above may be characterized by specific sequences of events, the sensor system 102 may also derive information about the events themselves or the dispensing system operation from the information embodied in the sensor signals (e.g., in the sensor signal pulse trains), comparison between the outputs of the sensors 80, 84, and externally determined or known information about the tablets and tablet flow direction.

Figure 13:
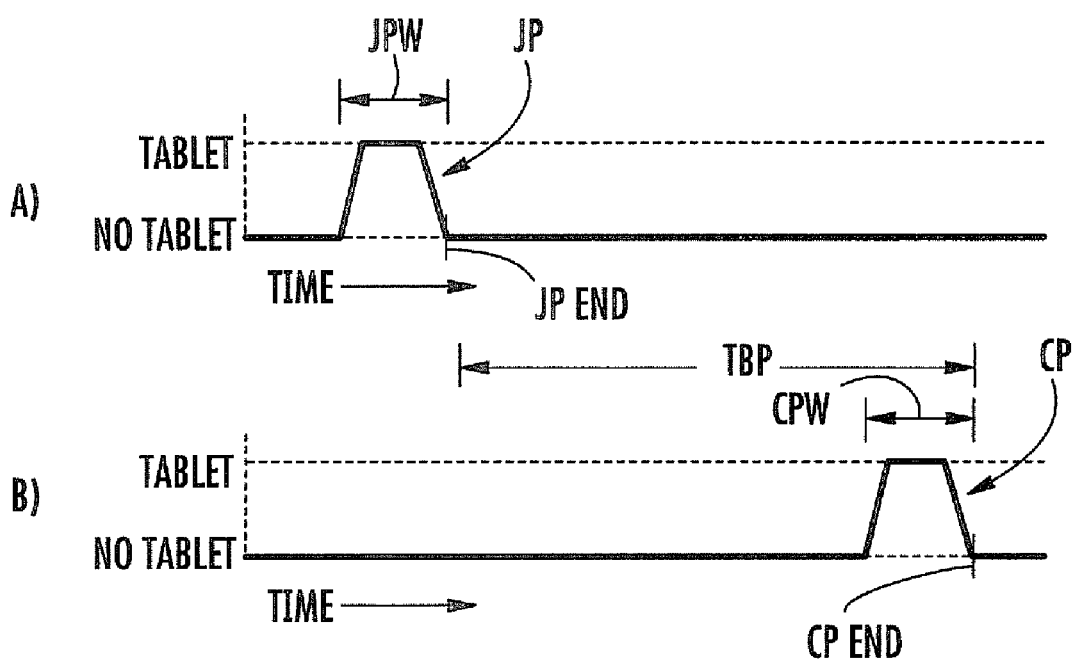

The sensor system 102 may allow for measurement of speed and time related to tablet dispensing. According to some embodiments, the length of a complete prescribed tablet (hereinafter, "Tablet Length") is known. With reference to FIG. 13, for each tablet dispensed through the channel 120, the controller 42 will receive a detection signal pulse JP from the entrance sensor 84 and a detection signal pulse CP from the exit sensor 80. The pulse JP has a duration or width JPW corresponding to the duration of occlusion of the sensor 84 by the tablet. Likewise, the pulse CP has a duration or width CPW corresponding to the duration of occlusion of the sensor 80 by the tablet. The controller 42 determines the velocity of each tablet through the outlet 124 (its "exit velocity") and the velocity of the tablet through the inlet 122 (its "entrance velocity") using the pulse widths JPW, CPW and the known Tablet Length. More particularly, the exit velocity can be calculated as:

Tablet Length/Pulse width CPW=exit velocity

The entrance velocity can be calculated as:

Tablet Length/Pulse width JPW=entrance velocity

Additionally, the controller can determine the velocity at which the tablet travels through the channel 120 (nozzle velocity) using the known distance ("sensor distance"; e.g., the distance D (FIG. 5)) between the operative trailing edge of the signal from the sensor 84 and the operative trailing edge of the signal from the sensor 80, and the measured time between pulses (TBP) (i.e., the duration between the end times CP End and JP End of the pulses CP and JP (i.e., the trailing edges of the pulses CP and JP), respectively). Using the trailing edges (CP End and JP End) may assist in determining when an event is over; however, the start times of the pulses CP, JP can be used instead. More particularly, the nozzle velocity can be calculated as:

sensor distance/(CP End−JP End)=nozzle velocity

From these measurements and prescribed values, the controller 42 can "learn" or determine the average exit velocity, the average entrance velocity, and the average nozzle velocity for tablets dispensed through the channel 120. These average values can be applied to specific events (i.e., dispensed tablets) to identify or evaluate additional characteristics of the events.

According to some embodiments, when the pulses CP, JP for a given tablet indicate that the tablet has passed through the channel 120 at the average nozzle velocity but one or both of the pulses CP, JP has a duration that is less than the average by more than a prescribed amount (e.g., one or two standard deviations), the controller 42 will identify the tablet as a partial tablet (i.e., a tablet having a length less than the prescribed or standard length for the tablets). Using the pulse duration or width measurements, the known tablet length, and the typical time between signal pulses, the sensor system 102 can determine the number of whole tablets and partial tablets that are dispensed, and even the sizes of the partial tablet fragments.

According to some embodiments, when a detection signal pulse CP, JP from a sensor 80, 84 has a duration that exceeds the average pulse for that sensor by more than a prescribed amount (e.g., one or two standard deviations), the controller 42 will identify an exception event. The controller 42 may further evaluate and catalog the exception event using this and additional available performance information. The controller 42 may assess the measured data and compare the measured data to the expected data for known specific events to identify a specific event corresponding to the measured data. Once the event or event type is identified, the controller may perform appropriate corrective action to the count, if any exists. The controller 42 may incorporate the states of the valves 142, 146 and/or the sequence in which the pulses from the sensors 80, 84 occurred in determining and cataloging the exception event.

The sensor system 102 can also provide real time statistics of dispensing performance for the bin 100, as well as a record of the performance of the bin 100.

While the sensor system has been described hereinabove with regard to the bin 100 and the dispensing system 40, sensor systems according to embodiments of the present invention may be used with bins and/or systems of other types and configurations. Sensor systems according to embodiments of the present invention may include sensors differently configured than the sensors 80, 84.

While embodiments employing forced gas drive mechanisms are described herein, other embodiments of the present invention may employ other drive mechanisms in place of or in addition to forced gas. For example, the pharmaceutical articles may be forced in the forward and/or reverse direction by vibration and/or gravity.

While various methods are described herein to identify dispensing fault conditions, these methods may also serve to confirm proper count conditions. More particularly, the lack of identification of a dispensing fault condition may be registered or affirm a valid count or count session. Accordingly, sensor systems as disclosed herein may provide improvements in count confidence.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention. Therefore, it is to be understood that the foregoing is illustrative of the present invention and is not to be construed as limited to the specific embodiments disclosed, and that modifications to the disclosed embodiments, as well as other embodiments, are intended to be included within the scope of the invention.

That which is claimed is:

1. A method for dispensing solid pharmaceutical articles using an apparatus including a housing and a sensor system, the housing defining a dispensing channel having a dispensing inlet and a dispensing outlet downstream of the dispensing inlet, the sensor system including first and second sensors spaced apart along the dispensing channel such that the second sensor is located downstream of the first sensor, the method comprising:
   forcing at least one article along a path through the dispensing channel;
   generating detection signals using the first and second sensors responsive to articles passing through the dispensing channel; and
   using the detection signals from the first and second sensors to monitor dispensing performance of the apparatus;
   wherein using the detection signals from the first and second sensors includes comparing the detection signals from the first and second sensors to determine whether a dispensing fault condition has occurred.

2. The method of claim 1 wherein the first sensor is located proximate the dispensing inlet and the second sensor is located proximate the dispensing outlet.

3. The method of claim 1 including counting the articles passing through the dispensing channel using at least one of the first and second sensors.

4. The method of claim 3 including:
counting the articles passing through the dispensing channel using the second sensor; and
detecting jams of the articles using the first sensor.

5. The method of claim 1 including:
forcing articles through the dispensing channel in a forward direction toward the dispensing outlet; and
identifying a preload dispensing fault condition responsive to detecting the presence of an article at the dispensing inlet using the first sensor prior to forcing the articles through the dispensing channel in the forward direction.

6. The method of claim 5 including, responsive to identifying the preload dispensing fault condition, forcing the article in the dispensing channel out of the dispensing channel in a reverse direction through the dispensing inlet.

7. The method of claim 1 including:
forcing articles through the dispensing channel in a forward direction toward the dispensing outlet; and thereafter
identifying a tandem dispensing fault condition responsive to receiving a continuous detection signal from the second sensor having a duration that is larger than a reference signal duration.

8. The method of claim 1 including:
forcing articles through the dispensing channel in a forward direction toward the dispensing outlet; and thereafter
identifying a collision dispensing fault condition responsive to detecting two apparent articles passing the first sensor and only a single corresponding apparent article thereafter passing the second sensor.

9. The method of claim 1 including:
forcing articles through the dispensing channel in a forward direction toward the dispensing outlet; thereafter
forcing articles in the dispensing channel in a reverse direction toward the inlet; and
identifying an aspiration dispensing fault condition responsive to detecting an article passing the second sensor while forcing the article through the dispensing channel in the reverse direction.

10. The method of claim 9 including subtracting the article from an article count responsive to identifying the aspiration dispensing fault condition.

11. The method of claim 1 including:
forcing articles through the dispensing channel in a forward direction toward the dispensing outlet; thereafter
forcing articles in the dispensing channel in a reverse direction toward the inlet; and
identifying an article reversal dispensing fault condition responsive to:
detecting an article passing the first sensor while forcing the articles through the dispensing channel in the forward direction; thereafter
detecting the article at least partially passing the second sensor; and thereafter
detecting the article passing the first sensor while forcing the articles through the dispensing channel in the reverse direction.

12. The method of claim 1 including using the detection signals from the first and second sensors to determine an average travel velocity for articles dispensed through the dispensing channel.

13. The method of claim 12 including using the determined average travel velocity and detection signals from at least one of the first and second sensors to identify a partial article dispensed through the dispensing channel.

14. The method of claim 12 including using the determined average travel velocity and detection signals from at least one of the first and second sensors to identify an exception event corresponding to a longer than average detection signal pulse.

15. The method of claim 1 wherein forcing at least one article along the path through the dispensing channel includes generating at least one drive gas flow using a flow generator to force the at least one article along the path through the dispensing channel.

16. The method of claim 15 including forcing the articles through the dispensing channel using a drive gas jet.

17. The method of claim 15 including positively controlling a positive pressure source to provide the at least one drive gas flow.

18. The method of claim 1 including dispensing the articles from a hopper chamber of the housing into the dispensing channel.

19. A method for dispensing solid pharmaceutical articles using an apparatus including a housing and a sensor system, the housing defining a dispensing channel having a dispensing inlet and a dispensing outlet downstream of the dispensing inlet, the sensor system including first and second sensors positioned along the dispensing channel, the method comprising:
forcing at least one article along a path through the dispensing channel;
generating detection signals using the first and second sensors responsive to articles passing through the dispensing channel; and
comparing the detection signals from the first and second sensors to determine whether a dispensing fault condition has occurred.

20. A method for dispensing solid pharmaceutical articles using an apparatus including a housing and a sensor system, the housing defining a dispensing channel having a dispensing inlet and a dispensing outlet downstream of the dispensing inlet, the sensor system including first and second sensors spaced apart along the dispensing channel such that the second sensor is located downstream of the first sensor, the method comprising:
forcing articles along a path through the dispensing channel in a forward direction toward the dispensing outlet;
generating detection signals using the first and second sensors responsive to articles passing through the dispensing channel; and
using the detection signals from the first and second sensors to monitor dispensing performance of the apparatus, including identifying a preload dispensing fault condition responsive to detecting the presence of an article at the dispensing inlet using the first sensor prior to forcing the articles through the dispensing channel in the forward direction.

21. The method of claim 20 including, responsive to identifying the preload dispensing fault condition, forcing the article in the dispensing channel out of the dispensing channel in a reverse direction through the dispensing inlet.

22. The method of claim 20 wherein the first sensor is located proximate the dispensing inlet and the second sensor is located proximate the dispensing outlet.

23. The method of claim 20 including counting the articles passing through the dispensing channel using at least one of the first and second sensors.

24. The method of claim 20 wherein forcing the articles along the path through the dispensing channel includes generating at least one drive gas flow using a flow generator to force the at least one article along the path through the dispensing channel.

25. The method of claim 24 including forcing the articles through the dispensing channel using a drive gas jet.

26. The method of claim 20 including dispensing the articles from a hopper chamber of the housing into the dispensing channel.

27. A method for dispensing solid pharmaceutical articles using an apparatus including a housing and a sensor system, the housing defining a dispensing channel having a dispensing inlet and a dispensing outlet downstream of the dispensing inlet, the sensor system including first and second sensors spaced apart along the dispensing channel such that the second sensor is located downstream of the first sensor, the method comprising:
   forcing articles along a path through the dispensing channel in a forward direction toward the dispensing outlet;
   generating detection signals using the first and second sensors responsive to articles passing through the dispensing channel; and
   using the detection signals from the first and second sensors to monitor dispensing performance of the apparatus, including, after forcing the articles through the dispensing channel in the forward direction, identifying a tandem dispensing fault condition responsive to receiving a continuous detection signal from the second sensor having a duration that is larger than a reference signal duration.

28. The method of claim 27 wherein the first sensor is located proximate the dispensing inlet and the second sensor is located proximate the dispensing outlet.

29. The method of claim 27 including counting the articles passing through the dispensing channel using at least one of the first and second sensors.

30. The method of claim 27 wherein forcing the articles along the path through the dispensing channel includes generating at least one drive gas flow using a flow generator to force the at least one article along the path through the dispensing channel.

31. The method of claim 30 including forcing the articles through the dispensing channel using a drive gas jet.

32. The method of claim 27 including dispensing the articles from a hopper chamber of the housing into the dispensing channel.

33. A method for dispensing solid pharmaceutical articles using an apparatus including a housing and a sensor system, the housing defining a dispensing channel having a dispensing inlet and a dispensing outlet downstream of the dispensing inlet, the sensor system including first and second sensors spaced apart along the dispensing channel such that the second sensor is located downstream of the first sensor, the method comprising:
   forcing at least one article along a path through the dispensing channel;
   generating detection signals using the first and second sensors responsive to articles passing through the dispensing channel; and
   using the detection signals from the first and second sensors to monitor dispensing performance of the apparatus, including using the detection signals from the first and second sensors to determine an average travel velocity for articles dispensed through the dispensing channel.

34. The method of claim 33 including using the determined average travel velocity and detection signals from at least one of the first and second sensors to identify a partial article dispensed through the dispensing channel.

35. The method of claim 33 including using the determined average travel velocity and detection signals from at least one of the first and second sensors to identify an exception event corresponding to a longer than average detection signal pulse.

36. The method of claim 33 wherein the first sensor is located proximate the dispensing inlet and the second sensor is located proximate the dispensing outlet.

37. The method of claim 33 including counting the articles passing through the dispensing channel using at least one of the first and second sensors.

38. The method of claim 33 wherein forcing at least one article along the path through the dispensing channel includes generating at least one drive gas flow using a flow generator to force the at least one article along the path through the dispensing channel.

39. The method of claim 38 including forcing the articles through the dispensing channel using a drive gas jet.

40. The method of claim 33 including dispensing the articles from a hopper chamber of the housing into the dispensing channel.

* * * * *